US008536518B2

(12) United States Patent
Kozole

(10) Patent No.: US 8,536,518 B2
(45) Date of Patent: Sep. 17, 2013

(54) ION MOBILITY SPECTROMETER TO MASS SPECTROMETER INTERFACE

(75) Inventor: Joseph Kozole, Brigantine, NY (US)

(73) Assignee: U.S. Department of Homeland Security, Washington, DC (US)

( * ) Notice: Subject to any disclaimer, the term of this patent is extended or adjusted under 35 U.S.C. 154(b) by 0 days.

(21) Appl. No.: 13/533,564

(22) Filed: Jun. 26, 2012

(65) Prior Publication Data

US 2012/0326023 A1 Dec. 27, 2012

Related U.S. Application Data

(63) Continuation of application No. 61/501,309, filed on Jun. 27, 2011.

(51) Int. Cl.
*H01J 49/42* (2006.01)
*H01J 49/26* (2006.01)
*B01D 59/44* (2006.01)

(52) U.S. Cl.
USPC ........... 250/281; 250/282; 250/287; 250/288; 250/290; 250/292

(58) Field of Classification Search
USPC .................. 250/281, 282, 288, 290, 292, 287
See application file for complete search history.

(56) References Cited

U.S. PATENT DOCUMENTS 6,992,284 B2 * 1/2006 Schultz et al. ................ 250/287
7,223,969 B2 * 5/2007 Schultz et al. ................ 250/290

OTHER PUBLICATIONS

Denson, S.; Ion Mobility Spectrometry Utilizing Micro Faraday Finger Array Detector Technology; IJIMS 5 (2002)3. 100-103p.
Hunka, D.; Ion Mobility Spectrometer/ Mass Spectrometer (IMS-MS); Sandia Report SAND2005-6908, p. 2-21, Jul. 2006.
Tang, K.; Two-Dimensional Gas-Phase Seperations Coupled to Mass Spectrometry for Analysis of Complex Mixtures; Anal. Chem. Oct. 1, 2005; 77(19): 6381-6388.

* cited by examiner

*Primary Examiner* — Nikita Wells
(74) *Attorney, Agent, or Firm* — Lavanya S. Ratnam; William Washington

(57) ABSTRACT

A method and apparatus are described herein for the interface of an ion mobility spectrometer (IMS) to a mass spectrometer (MS) that utilizes collisional focusing, through internal modification. Commercial standalone IMS instrumentation cannot be combined in tandem with a commercially available MS that utilizes collisional focusing due to the physics of the differentially pumped interface of the MS being an unsuitable environment for an IMS measurement. The invention provides for transfer of the ion beam from the IMS to the MS without distortion of the chemical species or temporal profile due to large scale collisions in the differentially pumped interface, by increasing the electric field strength between the orifice and skimmer, and decreasing the pressure in the differentially pumped interface, thereby reducing the number of background gas collisions encountered by the ion beam during transit from the IMS to the MS.

16 Claims, 11 Drawing Sheets

ION MOBILITY SPECTROMETER TO MASS SPECTROMETER INTERFACE

PRIORITY CLAIM

This Utility Patent Application claims the benefit of U.S. Provisional Application No. 61/501,309 filed on Jun. 27, 2011, the entirely of which is incorporated herein.

STATEMENT AS TO FEDERALLY SPONSORED RESEARCH

This invention was made with Government support under Contract DTFACT0400004 funded by the U.S. Department of Homeland Security. The Government has certain rights in this invention.

BACKGROUND OF THE INVENTION

1. Field of the Invention

This invention relates to a method and apparatus for interfacing an ion mobility spectrometer (IMS) to a mass spectrometer (MS) that utilizes collisional focusing. More specifically this invention is related to the internal modification of a standard configuration IMS and MS instrument, which will allow the two instruments to be joined in tandem and thereby achieve a greater selectivity and sensitivity of analysis over a single sample.

2. Background of the Invention

The use of improvised explosive devices (IEDs) for terrorist purposes will continue to be a threat to public safety for the foreseeable future. To help mitigate this threat, more than 15,000 explosive trace detectors (ETDs) are deployed at security checkpoints worldwide. The function of an ETD is to detect the presence of an explosive residue on a subject that has been in contact with an IED. Accordingly, the primary characteristics required of an ETD are selectivity and sensitivity.

Ion mobility spectrometry (IMS) is the analytical method most commonly implemented in ETD equipment. In IMS, the velocity of an ion though a buffer gas in the presence of an electric field is measured. Because the velocity of the ion is proportional to its reduced mass and cross-section, the ion is identified on the basis of its size. Moreover, because the ion is formed by efficient atmospheric pressure chemical ionization (APCI) processes, low limits of detection are observed in positive polarity for molecules with high proton affinities and in negative polarity for molecules with high electro-negativities. Consequent to these properties, IMS equipment that is operated in positive and negative polarity with ammonia and chlorine based reactant reagents has routinely demonstrated nanogram or better sensitivities for the detection of a suite of peroxide, nitro, and nitrate containing explosives.

While IMS has the selectivity and sensitivity needed to accurately detect trace amounts of explosives under a variety of conditions, opportunities for improvement exist regarding false positive and false negative responses. A false positive is typically attributed to the inability of IMS to differentiate an analyte molecule from an interferent molecule of a similar size, whereas, a false negative is typically attributed to the inability of APCI to ionize an analyte molecule in a competitive ionization environment. Further complicating the false negative rate is the constantly evolving threat matrix to which IMS must continuously adapt.

The most practical approach to decreasing the false response rates of IMS equipment is to modify the operating parameters of the instrument, such as buffer gas temperature, reactant reagent, electric field strengths, and detection algorithms, with the objective of increasing selectivity. These types of modifications are most effectively made using a detailed understanding of the gas phase ion chemistry that is intrinsic to the instrument being modified.

A detailed study of the ion chemistry of commercial. IMS based ETD equipment is not available in the literature.

For example, the ion species that are formed in these IMS devices during the analysis of typically encountered explosives and chemical interferents have not been identified with the certainty of mass spectrometry (MS). While information about sample and atmosphere composition and an understanding of gas phase ionization processes have provided informed estimates about the identities of these ions, the complexities of the reactions that occur at atmospheric pressure may lead to possible misidentifications when these types of assumptions are used.

For this reason, the most effective way to identify the ions in an IMS instrument with a high level of confidence is through direct mass measurements using a mass spectrometer, preferably a Tandem MS.

Although single unit IMS-MS combination instrumentation have been used in the field of ETD, such instrumentation is extremely expensive and produced in very limited quantity. The IMS/MS interface configuration of the invention described herein provides a practical apparatus and method for the interface of an easily obtainable COTS IMS and COTS MS detection system.

SUMMARY OF THE INVENTION

Briefly described, in an exemplary embodiment, the interface of the present disclosure overcomes the below-mentioned disadvantages and meets the recognized need for such a device.

The invention provides a method for combining an IMS instrument with a separate Commercial off the Shelf (COTS) MS instrument. Generally, an IMS instrument cannot be combined with a mass spectrometer that utilizes collisional focusing due to the physics of the differentially pumped interface of the mass spectrometer being an unsuitable environment for an IMS measurement.

Replacing the original skimmer in the standard configuration of the mass spectrometer with the skimmer of the invention alters the physics in the differentially pumped interface in such a way that the process of combining an IMS instrument to a mass spectrometer can be realized.

The invention alters the environment of the differentially pumped interface in such a manner that the process of combining an IMS instrument to a MS that utilizes collisional cooling can be easily realized, providing a simple, cost-efficient platform for obtaining ion mobility (IMS)—tandem mass spectrometry (MS) data.

These and other features and advantages of the device of the present disclosure will become more apparent to those ordinarily skilled in the art after reading the following Detailed Description of the Invention and claims in light of the accompanying drawing figures.

BRIEF DESCRIPTION OF THE DRAWINGS

The invention together with the above and other objects and advantages will be best understood from the following detailed description of the preferred embodiment of the invention shown in the accompanying drawings, wherein.

DETAILED DESCRIPTION OF THE INVENTION

Figure 1:
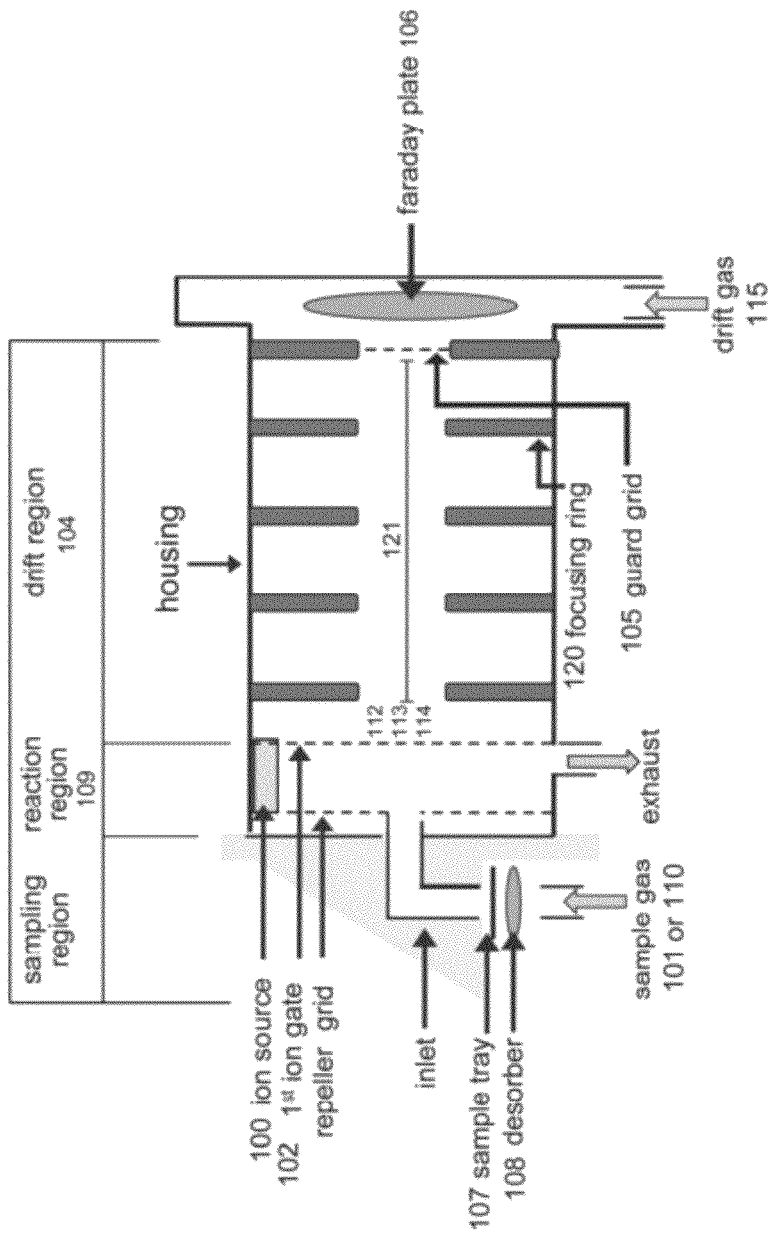
FIG. 1 is a schematic depiction of a representative commercial off-the-shelf (COTS) ion mobility spectrometer (IMS), in accordance with features of the present invention.

In describing exemplary embodiments of the IMS to MS interface of the present disclosure illustrated in the drawings, specific terminology is employed for the sake of clarity. The claimed invention, however, is not intended to be limited to the specific terminology so selected, and it is to be understood that each specific element includes all technical equivalents that operate in a similar manner to the described element.

The invention provides an interface between a Commercial off the Shelf (COTS) IMS based ETD and COTS MS, and provides a platform that can completely characterize the ion chemistry of this particular type of ETD. The invention is applicable to the integration of any IMS (or any other fast time-scale separation instrument) to any MS detection system that utilizes collisional focusing in its differentially pumped interface.

A general description of an ion mobility spectrometer and a mass spectrometer that utilizes collisional cooling are described below. Followed by a description of the apparatus and the procedure for integrating the apparatus into the two individual systems to develop a combined ion mobility mass spectrometry (IMS/MS) instrument.

Drift Tube Ion Mobility Spectrometer

The fundamental components of a typical drift tube ion mobility spectrometer are a reaction region with an ionization source, 100, and reaction reagent, 101, an ion gate, 102, a counter flow ambient pressure drift region, 104, a passive guard grid, 105, and a faraday plate detector, 106 (see FIG. 1).

To analyze a sample, 107, using a typical IMS instrument, a desorbed, 108, or vaporized sample is carried into the reaction region, 109, using an input flow of purified air, 110, and is ionized via its interaction with the ionization source and reactant reagent, 101.

Ions produced in the reaction region, 109, are transferred into the drift region in the form of ion packets by an electrostatic ion gate, 112, composed of a set of two grids, 113, 114, positioned orthogonal to the path of the ion beam.

In the drift region, the ion packets travel toward the guard grid, 105, under the influence of a uniform electric field and separate based on the velocity of the ions through a counter flow drift gas, 115, at ambient pressure.

After passing the guard grid, 105, the ions are detected using the faraday plate detector, 106, and the ion intensity is registered as a function of the drift time from the ion gate, 102, to the faraday plate, 106, to produce a mobility spectrum.

Examples of an IMS instrument include a Smith Detection Ionscan and a Morpho Detection Itemiser.

Mass Spectrometer with Collisional Focusing

Figure 2:
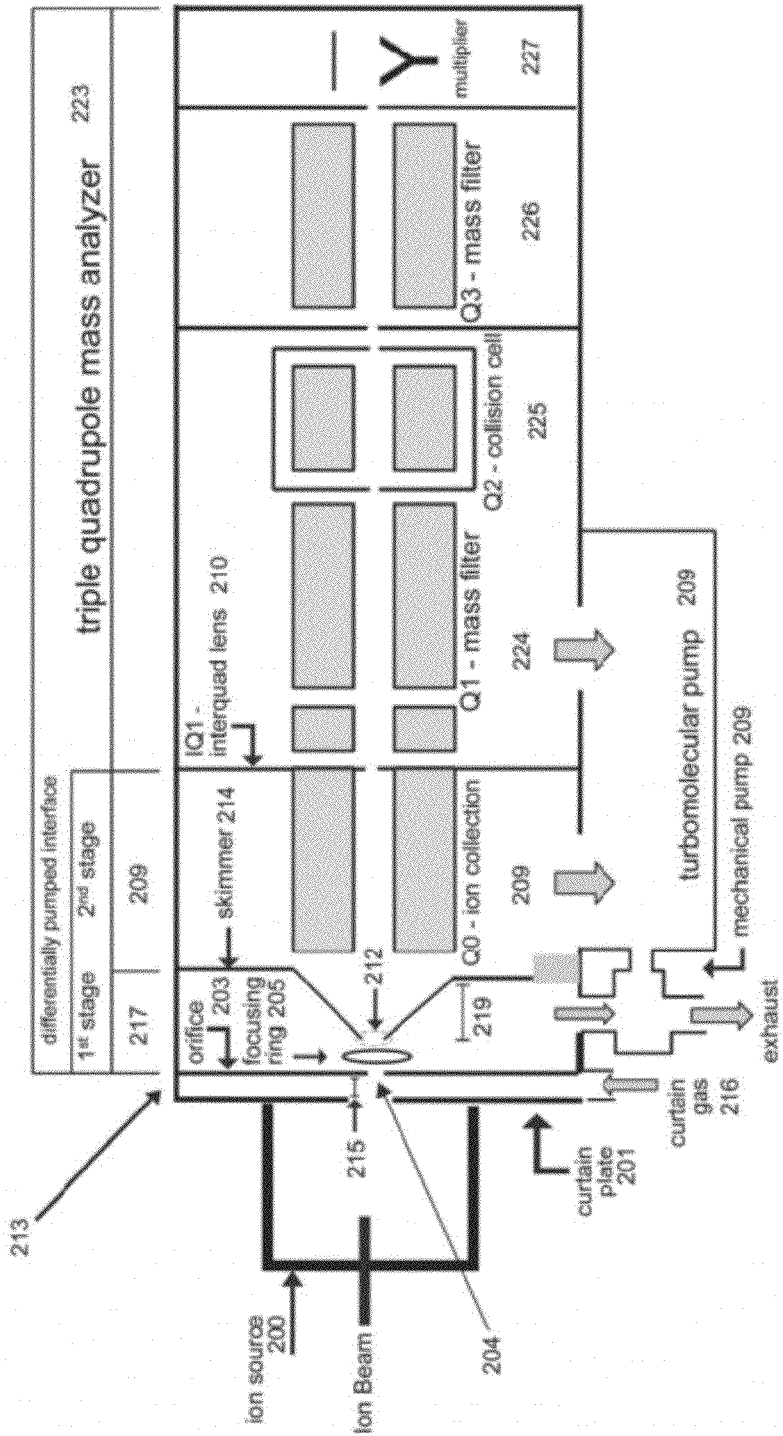
FIG. 2 is a schematic depiction of a representative COTS mass spectrometer (MS) with collisional focusing (i.e. an AB/SCIEX API 2000), in accordance with features of the present invention.

A typical mass spectrometer that utilizes collisional focusing is comprised of an ionization source, 200, a curtain plate, 201, a differentially pumped interface, 202, and a tandem mass analyzer with electron multiplier detector (see FIG. 2).

To analyze a sample using this type of mass spectrometer, the sample is ionized via the ionization source and is guided into the differentially pumped interface by the voltage applied to the curtain plate, 201. The differentially pumped interface is divided into two separately pumped stages.

The first stage is composed of an orifice, 203, with a pinhole, 204, a focusing ring, 205, and a skimmer, 206, and is evacuated using a mechanical pump, 207, while the second stage is composed of a radio frequency (rf) only quadrupole (Q0), 209, and an interquad lens (IQ1), 210, and is evacuated using a turbomolecular pump, 211.

The ion beam is entered into the first stage through the pinhole, 204, of the orifice, 203, and is directed into the hole, 212, of the skimmer, 206, by voltages applied to the orifice, 203, focusing ring, 205, and skimmer, 206. A typical pinhole size in the orifice electrode is between 25 and 300 µm.

In the second stage (the Q0 region), 209, the trajectory of the ion beam is dampened onto the central axis of Q0 by collisions with the background gas (i.e. by collisional focusing) and is guided into the tandem mass analyzer by voltages applied to the skimmer, 206, Q0, 209, and IQ1, 210. In the tandem mass analyzer, the ion beam is filtered and detected to produce a mass or tandem mass spectrum.

Examples of a mass spectrometer that utilizes collisional focusing in its differentially pumped interface include an AB/SCIEX API 2000, API 3000, and Q-STAR.

Preparation of a Drift Tube Ion Mobility Spectrometer for Integration to a Mass Spectrometer with Collisional Cooling.

Figure 1A:
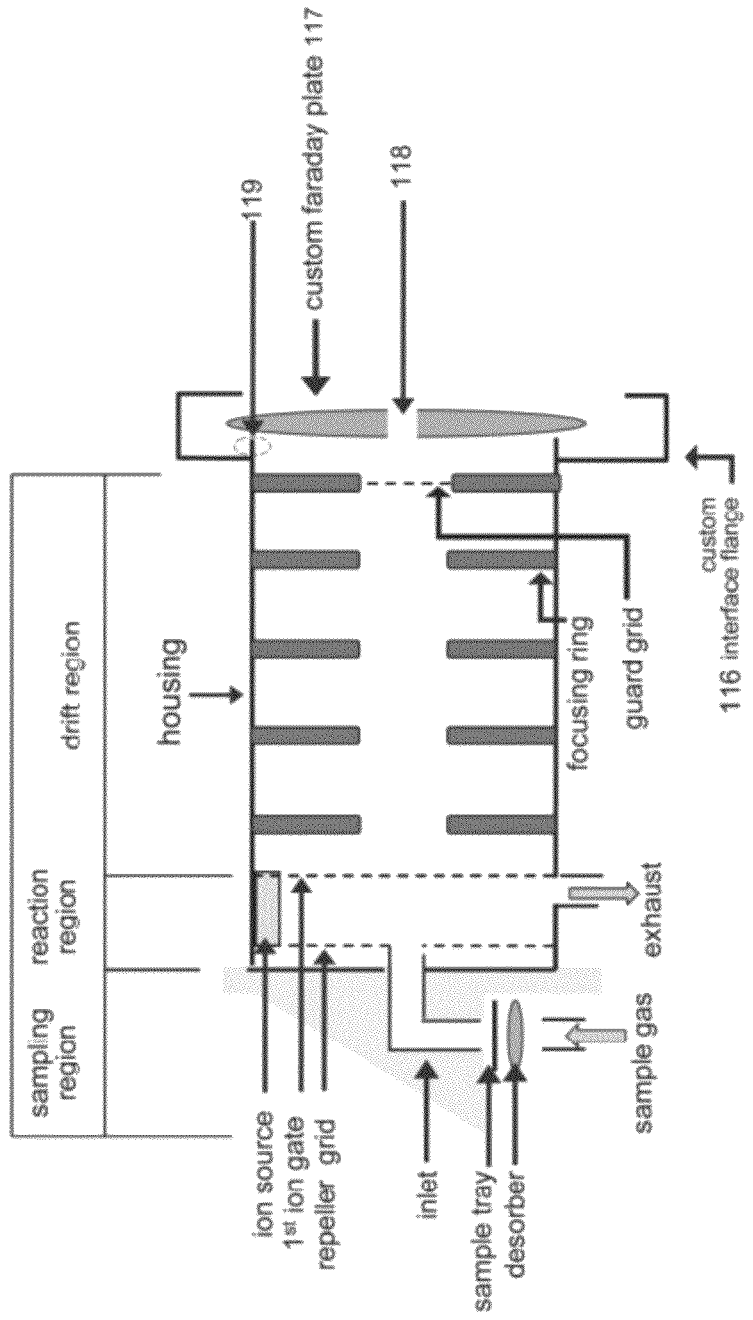
FIG. 1A is a schematic depiction of the modifications made to a standard IMS configuration in preparation for integration to a standard configuration mass spectrometer in accordance with features of the present invention.

To prepare an IMS instrument for integration to a mass spectrometer, the faraday plate detector, 106, and the portion of the IMS housing located after the guard grid, 105, are removed from the IMS instrument. The guard grid, 105, end of the IMS housing is then hermetically connected to an interface flange, 116, designed to attach to the atmospheric pressure interface (i.e. front-end) of the mass spectrometer in place of the curtain plate, 201. A new faraday plate, 117, constructed with a centered hole, 118, for passing a portion of the ion beam to the mass spectrometer is positioned after the guard grid, 105, on the mass spectrometer side of the custom interface flange, 116, and is electrically insulated using insulators, 119, made from polytetrafluoroethylene, aluminum oxide or other non-conductive material. The hole size in the faraday plate may range from 2 to 10 mm. An illustration of the modifications made to the IMS instrument is shown in FIG. 1A.

Preparation of a Mass Spectrometer with Collisional Focusing for Integration of a Drift Tube Ion Mobility Spectrometer Front-End.

Figure 2A:
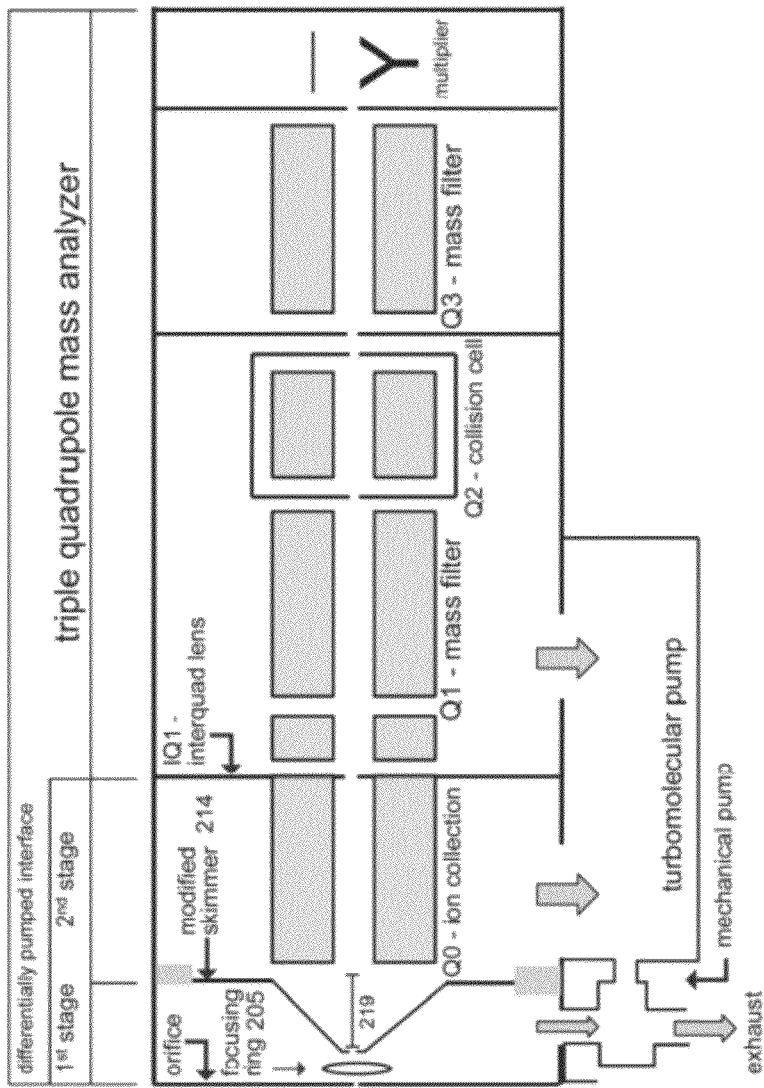
FIG. 2A is a Schematic depiction of the modifications made to a COTS MS (that utilizes collisional focusing) in preparation for the integration of an IMS front-end modified correspondingly to FIG. 1A.

To prepare a mass spectrometer that utilizes collisional focusing for integration of an IMS front-end, both the ionization source, 200, and curtain plate, 201, are removed from the atmospheric pressure interface, 213, of the mass spectrometer. Additionally, the skimmer, 206, in the standard configuration of the mass spectrometer is replaced with the modified skimmer, 214, of the invention (see Description of Modified Skimmer). An illustration of the modifications made to the MS is shown in FIG. 2A.

Integration of the Modified Drift Tube Ion Mobility Spectrometer to the Modified Mass Spectrometer.

Figure 3:
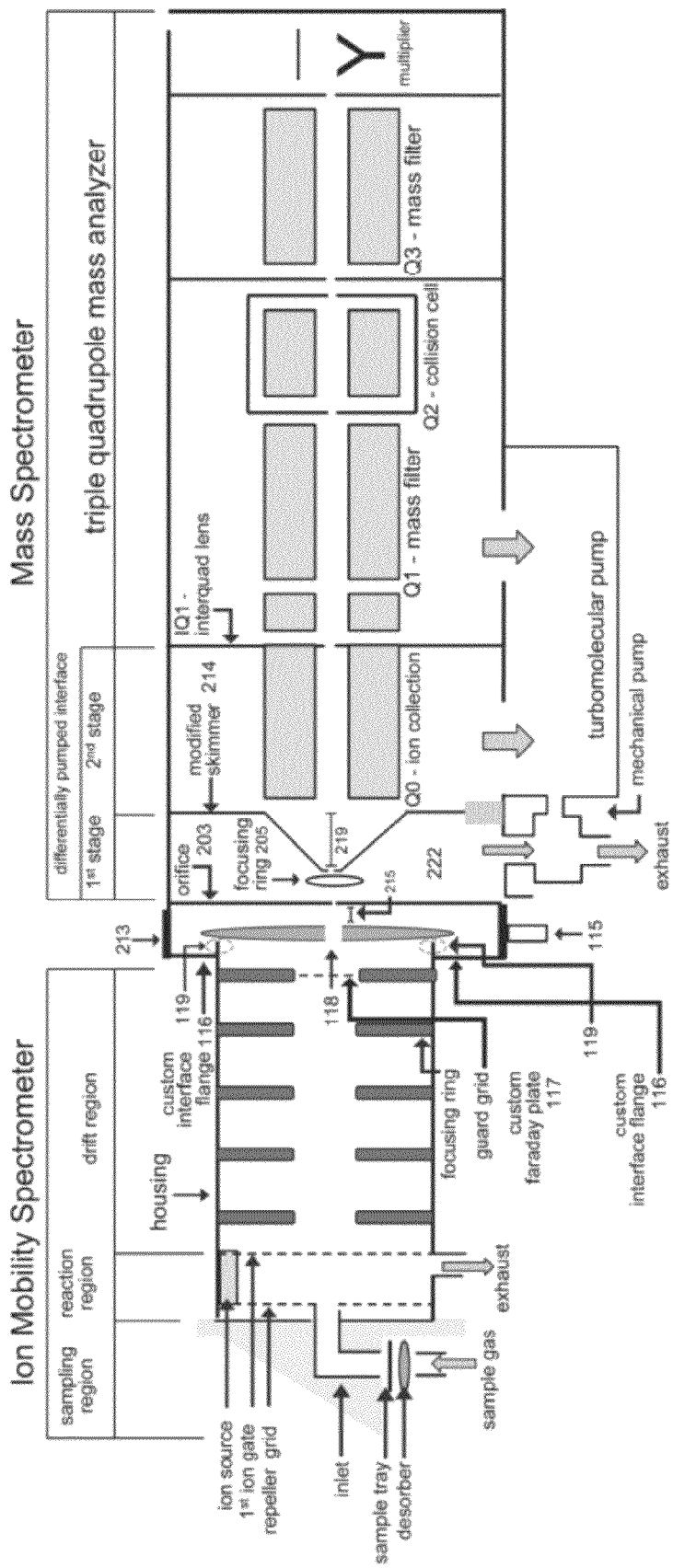
FIG. 3 is a Schematic depiction of a combined/interfaced IMS/MS instrument.
Figure 4:
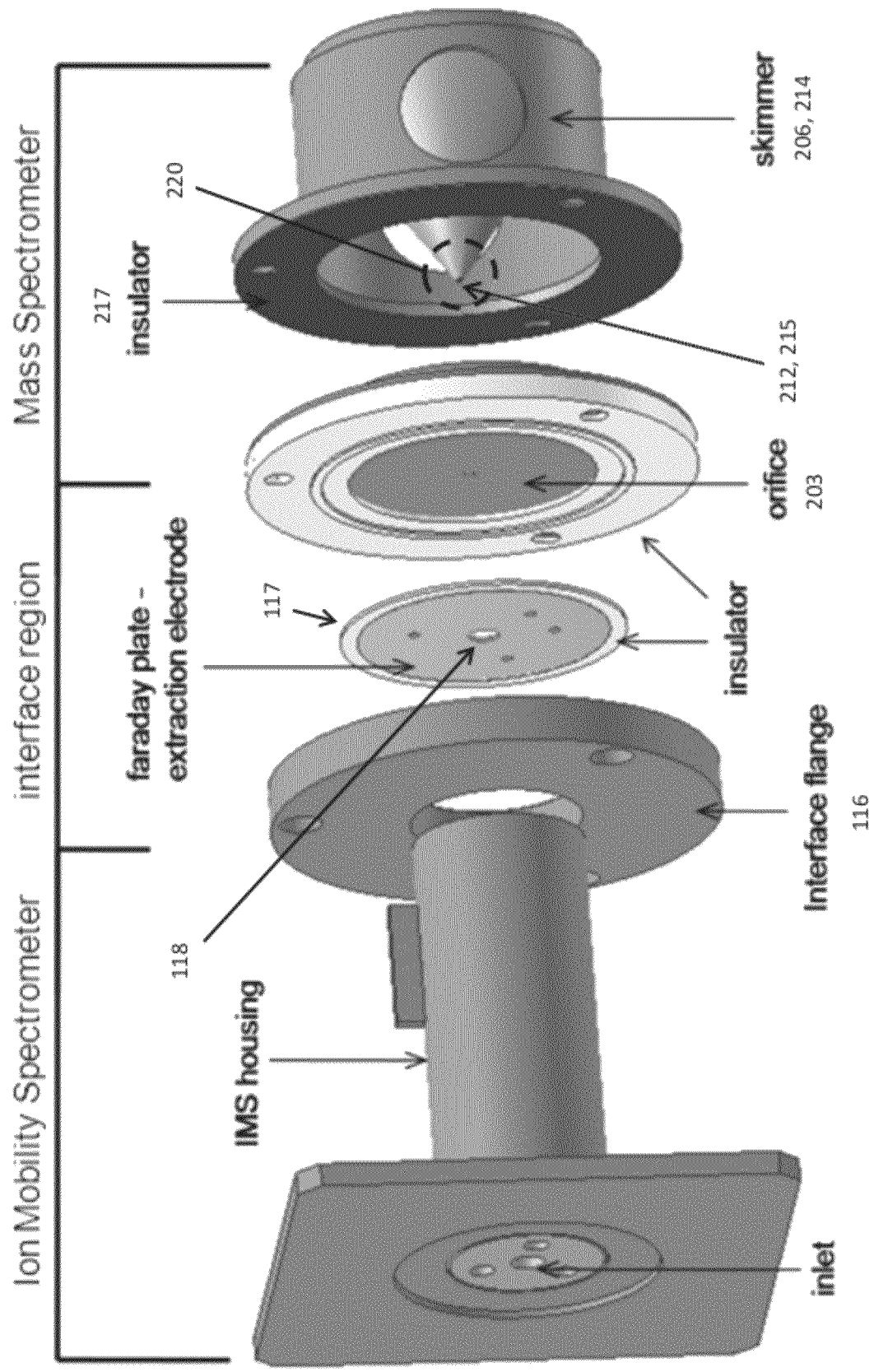
FIG. 4 is an enlarged area view of the integration region between the IMS and MS instrumentation.

To integrate the modified IMS to the modified MS, the customized interface flange, 116, (with IMS housing, 100, and custom faraday plate, 100) is attached to the atmospheric pressure interface, 213, of the mass spectrometer (in place of the curtain plate, 201) such that the hole, 118, in the custom faraday plate, 117, is positioned immediately (2-15 mm) before the pinhole, 215, in the orifice, 203 (see FIG. 3 and FIG. 4).

The customized faraday plate, 117, serves a dual function. The custom faraday plate, 117, is connected to a current preamplifier to detect the ion beam and measure a mobility spectrum and/or to a power supply to bias the electrode and extract the ion beam from the IMS instrument into the mass spectrometer. The drift gas, 115, for the IMS instrument is introduced into the region between the custom faraday plate, 117, and the orifice, 203, using the original inlet for the curtain gas, 216, on the mass spectrometer. Typical flow rates into the region between the faraday plate and orifice is between 650 and 2000 cc/min, for which 50 to 1000 cc/min flows into the IMS instrument.

Modification of Skimmer

A schematic of an IMS to MS interface where the mass spectrometer (in its standard configuration) utilizes collisional focusing is shown in FIG. 4. The modified skimmer, 214, of the invention replaces the original skimmer, 206, located between the first, 217, and second (Q0 region) 209, pumping stages of the differentially pumped interface of the mass spectrometer. The function of the differentially pumped interface is to transfer the ion beam from atmospheric pressure to the vacuum of the mass spectrometer.

The differentially pumped interface in the standard configuration of the mass spectrometer is not suitable to an IMS front-end. Specifically, the ion packet from the IMS instrument is broadened in the Q0 region of the differentially pumped interface due to collisional focusing, i.e. dampening of the ion packet onto the axis of the mass spectrometer through collisions with the background gas. Moreover, the first pumping stage of the differentially pumped interface does not include the capability to selectivity gate a portion of the ion beam from the IMS instrument into the mass spectrometer.

Figure 5:
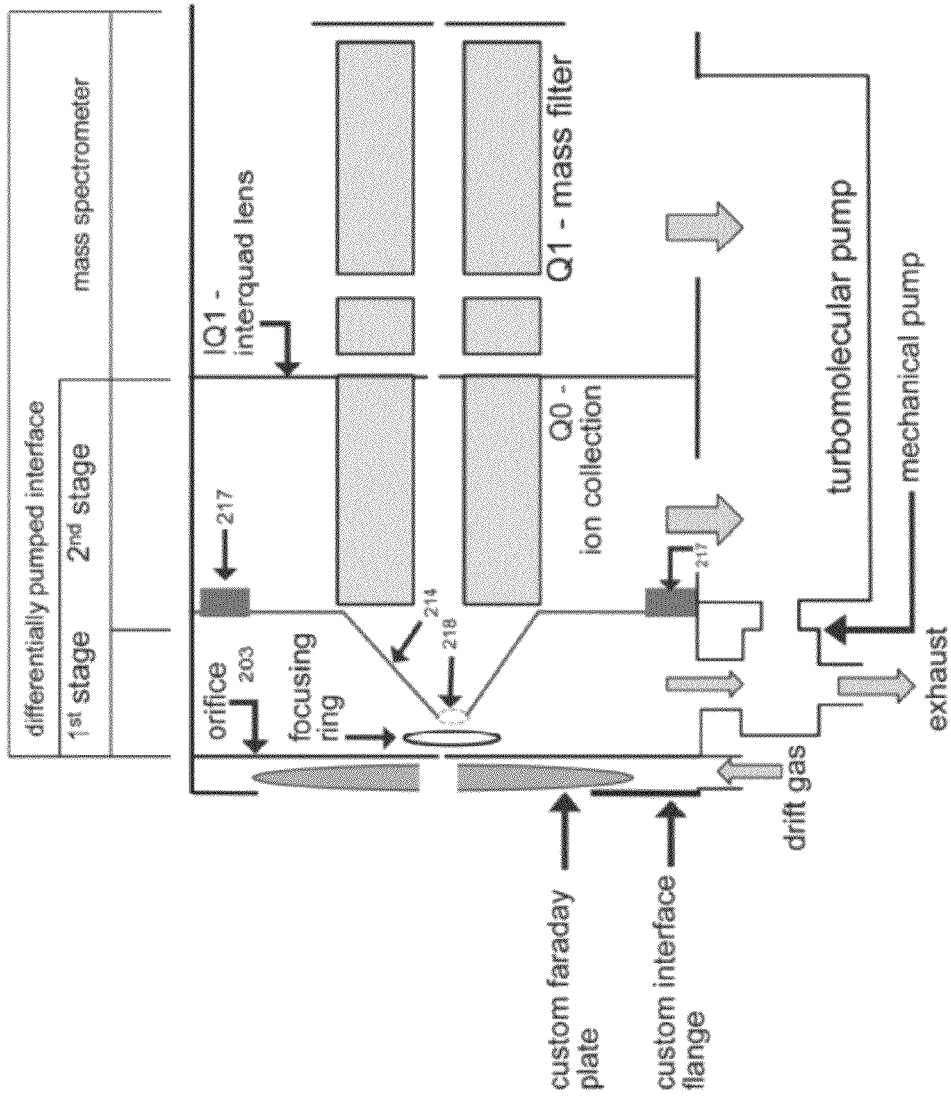
FIG. 5 is a schematic depiction of the two modifications made to the original skimmer configuration in the IMS/MS instrument. The first shows electrical isolation of the skimmer from the chamber of the MS; the second modification is through reduction of the skimmer hole diameter.

To address the above issues, a skimmer, 206, in the standard confirmation of the mass spectrometer may be modified in three different ways (FIG. 5). These modifications eliminate the broadening of the ion packet due to collisional focusing by increasing the electric field strength and decreasing the pressure in the Q0 region of the differentially pumped interface. Moreover, these modifications add ion beam gating capabilities to the differentially pumped interface by altering the voltages applied to the electrodes in the first pumping stage.

In the first modification (FIG. 5), the skimmer is electrically isolated from the chamber, 217, of the mass spectrometer using polytetrafluoroethylene, polyimide, or other non-conductive material to allow the electrode to be biased by an external power supply. This modification permits the electric field strength between the skimmer and Q0 to be tuned to a value larger than the standard configuration of the mass spectrometer, i.e. to a value between ±0 V/cm to 100 V/cm. This modification also permits the electric field between the orifice, 203, and the skimmer, 214, to be used as an ion gate for the mass spectrometer. For negative ion detection, the ion gate is closed when the skimmer, 214, is biased to a potential that is −200 to −20 V relative to the orifice, 203, and is open when the skimmer, 214, is biased to a potential that is −20 to +12 V relative to the orifice, 203. For positive ion detection, the ion gate is closed when the skimmer, 214, is biased to a potential that is +200 to +20 V relative to the orifice, 203, and is open when the skimmer, 214, is biased to a potential that is +20 to −12 V relative to the orifice.

In the second modification (FIG. 5), the standard skimmer, 206, configuration is modified to have a smaller opening, 218.

Figure 6:
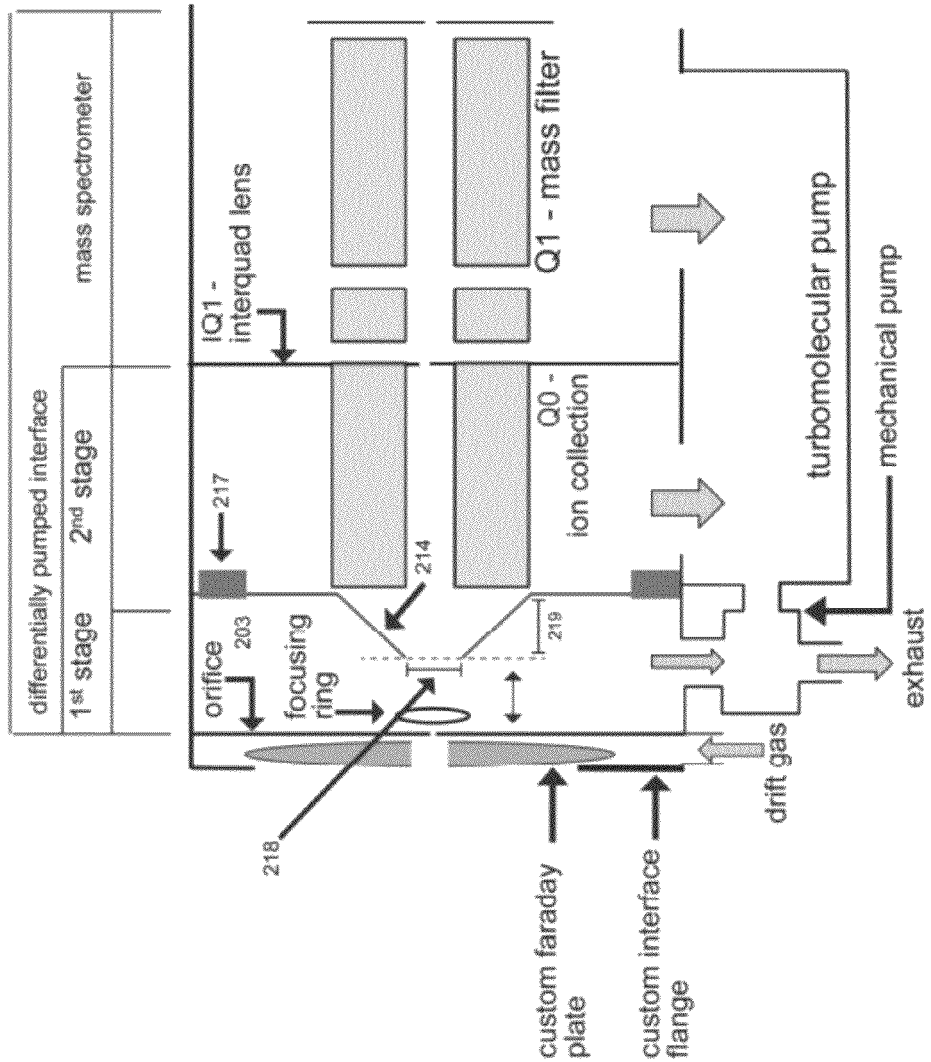
FIG. 6 is a schematic depiction of preferred embodiment of a conical modified skimmer. Where the skimmer is in electrical isolation from the chamber of the MS, and the length of the skimmer has been shortened.
Figure 7:
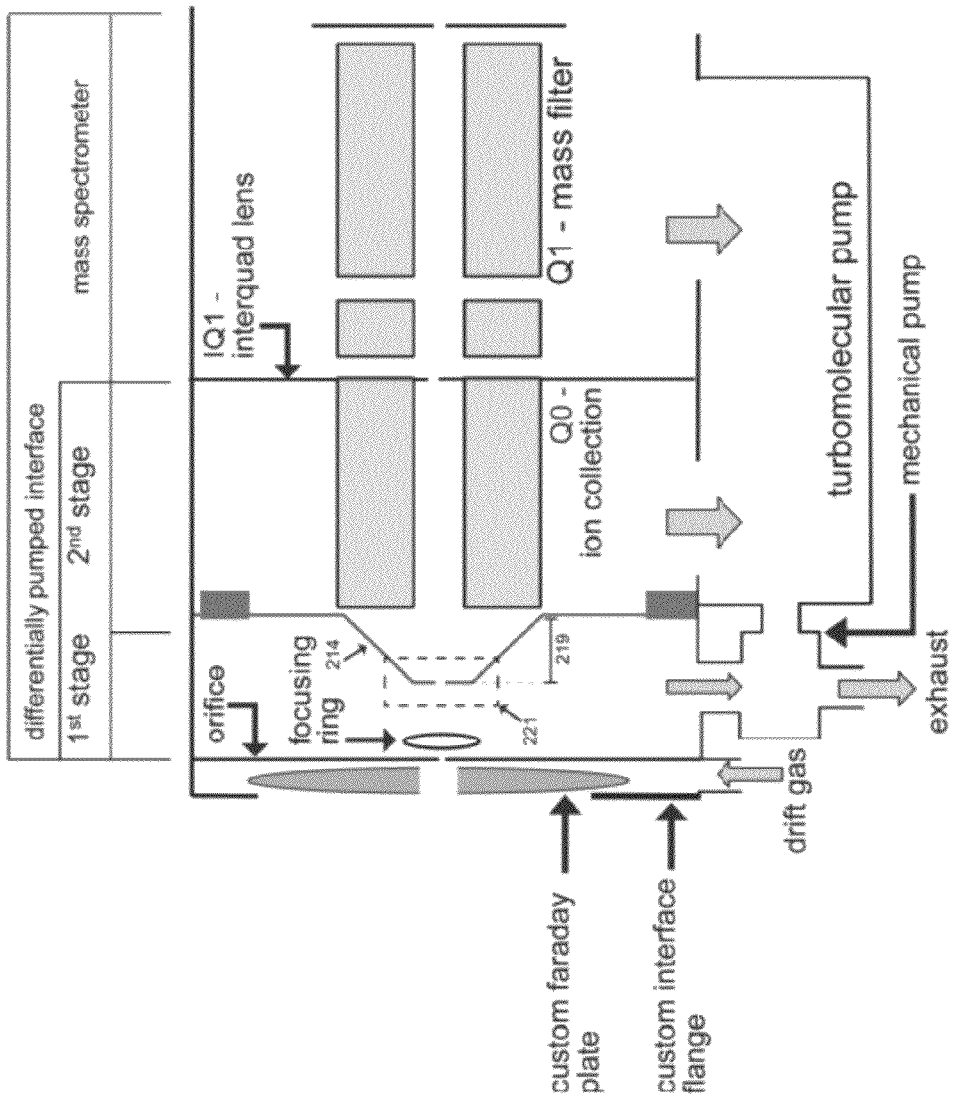
FIG. 7 shows an alternative embodiment of the skimmer where the tip has been flattened and shortened.

And for the third modification (FIG. 6) the opening, 218, of the skimmer, 214, is positioned farther away from the orifice, 203. For the MS model of the preferred embodiment, the opening, 218, in the skimmer, 214, was changed from 1090 µm to 400 µm whereas the length of the skimmer, 219, was shortened by 3 mm. However, a skimmer opening between 200 µm and 800 µm as well as a distance between the orifice and skimmer ranging from 4 to 10 mm is also acceptable for the configuration. A decrease of approximately a factor of 3 for the opening in the skimmer was made to decrease the pressure in Q0 by approximately a factor of 10. Pressure within the MS is proportional to skimmer opening size according to a $r^2$ relationship (i.e. $3^2$=9 (or approximately 10)). However, any decrease in the skimmer orifice size resulting in the pressure in the Q0 region being reduced to between 0.1 and 2 mtorr is acceptable. The length of the skimmer, 219, is shortened to a length that does not interfere with the Q0 quadrupole operation. All other physical dimensions of the standard skimmer, 206, configuration are left unchanged. These modifications decrease the pressure in the Q0 region by decreasing the amount of gas flow from the first pumping stage into the Q0 region. The tip of the skimmer, 221, should be conical in shape but may be flat in an alternative embodiment (FIGS. 7). The preferred (conical) modified skimmer is illustrated in FIGS. 5 & 6. Collectively, the modifications to the standard skimmer, 206, configuration make the differentially pumped interface of a mass spectrometer that utilizes collisional cooling suitable to an IMS front-end.

Operating Modes: Continuous Ion Flow: Mass-Selected Ion Mobility Single Gate: or Selected Mobility Monitoring Dual Gate In the continuous ion flow mode, both the ion gate in the IMS instrument (the first ion gate), 102, and the ion gate in the MS (the second ion gate), 222, are constantly held in the open position, permitting the ions formed in the reaction region of the IMS instrument to pass unrestricted into the mass spectrometer. This continuous flow of ions is analyzed by operating the mass analyzer in either the scan only mode or the product ion scan mode to acquire mass and tandem mass spectra.

In the mass-selected ion mobility mode (or tuned ion mobility mode), the first ion gate is opened for a finite period of time to allow a packet of ions into the drift region of the IMS instrument while the second ion gate, 222, is constantly held in the open position to allow the ion packet to pass unrestricted into the mass spectrometer. The mass analyzer is operated in the SIM mode to detect only the ions in the packet with a particular m/z. The ion intensity at the electron multiplier for the ion of interest is registered as a function of the drift time to produce a mass-selected ion mobility spectrum. The ion intensity is registered using a high Speed digitizer (National Instruments Model PXI 5124/512, Austin, Tex.) with custom written LabVIEW code (National Instruments) while the raw mobility spectra are processed using Igor Pro 6.2.

In the selected mobility monitoring mode, the first ion gate, 102, is opened for a finite period of time to allow a packet of ions into the drift region of the IMS instrument while the second ion gate, 222, is opened after a specified time delay for the same duration as the first ion gate: The time delay is selected to permit only the portion of the ion packet with a particular mobility range to pass into the mass spectrometer. This mobility filtered ion population is analyzed by operating the mass analyzer in either the scan only mode or the product ion scan mode. The time delay between the opening of the first, 102, and second ion gate, 222, is controlled using a data acquisition board (National Instruments Model PXI 6259) with custom written LabVIEW code while the voltage waveform applied to the second ion gate is generated using an arbitrary waveform generator (TEGAM, Inc. Model 2720A, Geneva, Ohio) and a voltage-to-voltage amplifier (TEGAM, Inc. Model 2340).

Preferred Configuration; Ion Mobility Spectrometer and Triple Quadropole Mass Spectrometer A schematic depiction of the interfaced IMS/MS instrumentation is shown in FIG. 3. The detection apparatus consist of three primary parts: an IMS based ETD, an interface region containing the subject invention, and a triple quadruple MS. The IMS based ETD used in the IMS/MS embodiment is an Ionscan 400B® (Smiths Detection Inc, Ontario, Canada).

The Ionscan® was selected because it is a commercially available ETD regularly deployed at security checkpoints. The Ionscan® used in the invention is operated using the same typical operation parameters as an Ionscan® that would be deployed at a security checkpoint. The electric field strengths, pressures, temperatures, and gas flows for the negative polarity operation of an Ionscan® with typical operation parameters are summarized in table 1.

TABLE 1

| Parameter | Value | Unit |
|---|---|---|
| Electric Field Strengths | | |
| drift region | 257 | V/cm |
| Pressures | | |
| reaction region/drift region | 760 | torr |
| Temperatures | | |
| desorber | 205 | ° C. |
| inlet | 245 | ° C. |
| reaction region/drift region (housing) | 115 | ° C. |

TABLE 1-continued

| Parameter | Value | Unit |
|---|---|---|
| reaction region/drift region (gas) | 111 | ° C. |
| Gas Flows | | |
| sample gas | 250 | cc/min |
| drift gas | 300 | cc/min |

Purified air (5-25 ppm water and 50-100 ppm carbon dioxide) was used as the sample and drift gases, hexachloroethane was used as the reaction reagent, and 4-nitrobenzonitrile was used as the internal calibrant.

The fundamental components of the Ionscan® IMS instrument are a thermal desorber, 108, and a metal cylindrical housing that contains a reaction region with a $^{63}$Ni radiation source, 100, and hexachloroethane reagent, 101, an ion gate, 102, a counterflow ambient pressure drift region, 121, and a faraday plate detector, 106. To introduce a sample into the IMS instrument, a filter dosed with particulate analyte is inserted into the thermal desorber, 107, 108, the particulate is vaporized, and the vapor is carried into the reaction region using a flow of purified air, 110. In the reaction region, 109, chloride reactant ions, which are generated by the interaction of $^{63}$Ni beta radiation with purified air and hexachloroethane reagent, 101, react with the vapor phase analyte molecules to form product ions. The reactant and product ions are transferred into the drift region in the form of ion packets by an electrostatic ion gate composed of a set of two grids, 113, 114, positioned orthogonal to the path of the ion beam. The ion gate is closed when the potential difference between the two grids is 18 V and is open when the two grids are held at the same potential. The drift region is composed of a stacked electrode assembly of several focusing rings, 120, and a passive guard grid, 105, separated by insulating spacers, and high temperature resistors. In the drift region, the ion packets travel toward the guard grid, 105, under the influence of a uniform electric field and separate based on the velocity of the ions through a counterflow drift gas of purified air. After passing the guard grid, the ions are detected using either the faraday plate, 117, or the mass spectrometer and the ion intensity is registered as a function of the drift time to produce a mobility spectrum. To calculate reduced mobility, the drift time of the analyte is normalized to the drift time of the internal calibrant 4-nitrobenzonitrile. The purified air used for the sample and drift gases was in-house air treated with a purge gas generator (Parker Balston Model 75, Haverhill, Mass.) and a purified air cartridge (Smiths Detection, Inc). The purified air had a moisture content of 5-25 ppm as measured by a moisture analyzer (General Electric Moisture Monitor Series 3, Skaneateles, N.Y.) and a carbon dioxide content of 50-100 ppm as measured by a carbon dioxide transmitter (Vaisala Series GMT 220, Helsinki, Finland). The operation of the IMS instrument was primarily controlled using the control and monitoring electronics module of the Ionscan®. The components not controlled using the electronics module include the temperature of the IMS housing, which is heated using insulated heating tape (BriskHeat, Columbus, Ohio) and a variable transformer, (ISE, Inc, Maumee, Ohio), the flow rates of the sample and drift gases, which are controlled using mass flow controllers (Sierra Instruments Model 100, Monterey, Calif.), and the step motor for the desorbel, which is controlled using a custom printed circuit board.

An API 2000® (Applied Biosystems/MDS SCIEX, Ontario, Canada, see FIG. 2) was selected as the preferred mass spectrometer (MS) in the IMS/MS combination because it has atmospheric sampling and tandem MS capability. The API 2000® is comprised of two main parts: a differentially pumped interface, 202, which is used to transfer the ion beam from atmospheric pressure to the vacuum of the mass spectrometer and a triple quadrupole mass analyzer, 223, (comprised of a mass filter (Q1), 224, a collision cell (Q2), 225, a second mass filter (Q3), 226, and an electron multiplier detector, 227) which is used to filter and detect the ion beam. The voltages, pressures, and temperatures for the negative polarity operation of the API 2000® are summarized in table 2.

TABLE 2

| Parameter | Mass and MS/MS spectra | | Mass-selected ion mobility spectra | |
|---|---|---|---|---|
| | Value | Unit | Value | Unit |
| Dimensions | | | | |
| distance from guard grid to faraday plate | 1.4 | mm | 1.4 | mm |
| distance from faraday plate to orifice | 4.5 | mm | 4.5 | mm |
| distance from orifice to | 3.3 | mm | 6.3 | mm |
| faraday plate hole size | 6.0 | mm | 6.0 | mm |
| orifice hole size | 254 | μm | 254 | μm |
| skimmer hole size | 1100 | μm | 400 | μm |
| Voltages | | | | |
| interface flange | ground | — | ground | — |
| guard grid | −90 | V | −90 | V |
| faraday plate/extraction | −75 | V | −75 | V |
| orifice | 5 | V | −20 | V |
| skimmer | 10 | V | −13 | V |
| Q0 | 12 | V | 12 | V |
| IQ1 | 13 | V | 22 | V |
| Pressures | | | | |
| 1$^{st}$ differentially pumped stage | 1 | torr | 1 | torr |
| 2$^{nd}$ differentially pumped stage (Q0 region) | $8 \times 10^{-3}$ | torr | $1 \times 10^{-3}$ | torr |
| mass spectrometer | $8 \times 10^{-1}$ | torr | $4 \times 10^{-1}$ | torr |
| Temperatures | | | | |
| orifice | 115 | °C | 100 | °C |

During the operation of the IMS/MS instrument, the mass analyzer is operated in the scan only mode to obtain a mass spectrum, the product ion scan mode to obtain a tandem mass (MS/MS) spectrum, and the selected ion monitoring (SIM) scan mode to obtain a mobility spectrum for a particular m/z. The mass and MS/MS spectra are recorded using the Analyst software (Applied Biosystems/MDS SCIEX) and are processed using Igor.Pro 6.2 (WaveMetrics, Portland, Oreg.).

The mass spectrometer of the API 2000® is primarily controlled using the API 2000® system electronics with the Analyst software. The components not controlled using the system electronics are the voltages applied to the orifice, the focusing ring, 205, and the skimmer, 214, which are applied using external power supplies (Spellman Model 230) to permit a larger voltage range to be used. Although the API 2000 is used in the preferred embodiment, the modified skimmer, 214, of the invention is applicable to any mass spectrometer that utilizes collisional focusing.

To establish the utility of the IMS/MS configuration the mass-to-charge ratios, collision-induced dissociation pathways, and reduced mobility values for the ion species formed during the analysis of the explosive standard TNT were measured. These measurements were obtained by operating the IMS/MS instrument in the continuous ion flow mode to acquire mass and MS/MS spectra, the mass-selected ion mobility mode to acquire mobility spectra for the ions of interest, and the selected mobility monitoring mode to acquire mass and MS/MS spectra for the individual peaks in the mobility spectra.

To construct the interface, the faraday plate, 106, and the portion of the IMS housing located after the guard grid, 105, were removed from the IMS instrument of the Ionscan®. Because the removed portion of the IMS housing contained the voltage and exhaust feedthroughs for the IMS instrument, replacement feedthroughs were added to the portion of the IMS housing that remained. After its modification, the guard grid, 105, end of the IMS housing was hermetically connected to a custom interface flange, 116, which was constructed from stainless steel and designed to attach to the atmospheric pressure interface, 213, of the API 2000®. A custom faraday plate, 117, which was constructed from gold plated stainless steel and with a centered hole, 118, for passing a portion of the ion beam to the mass spectrometer, was positioned after the guard grid, 105, on the mass spectrometer side of the interface flange, 116, and was electrically insulated using insulators, 119, made from polytetrafluoroethylene (PTFE) and polyimide. The curtain plate was removed from the mass spectrometer and the interface flange was attached in its place such that the hole, 118, in the faraday plate was positioned immediately before the pinhole, 204, in the orifice, 203, and the IMS housing and interface flange were electrically grounded. Electric contact was made with the faraday plate, 117, using the original feedthrough for the curtain plate, 201, on the mass spectrometer.

The faraday plate, 117, can be connected to a current preamplifier (Stanford Research Systems Model SR 570, Sunnyvale, Calif.) to detect the ion beam and measure a mobility spectrum or to a power supply (Spellman Model 230, Hauppauge, N.Y.) to bias the electrode and extract the ion beam from the IMS instrument into the mass spectrometer. The faraday plate, 117, is used as an extraction electrode in all operating modes where the mass spectrometer is used to detect the ion beam. Also in the design, the purified air for the drift gas is introduced into the interface region, 213, between the faraday plate and the orifice using the original inlet for the curtain gas on the mass spectrometer. Because a portion of the gas is pulled through the pinhole, 204, of the orifice, 203, and into the vacuum of the mass spectrometer, the total gas flow introduced into the interface region is 900 cc/min, 600 cc/min of which flows into the mass spectrometer and 300 cc/min of which flows into the IMS instrument and serves as the drift gas. The skimmer, 214, in the preferred embodiment was modified in three different ways; by insolating the skimmer from the housing of the mass spectrometer, 217, by changing the opening in the skimmer from 1090 μm to 400 μm, 218, and by shortening the length of the skimmer by 3 mm, 222. All other physical dimensions of the standard skimmer configuration were left unchanged.

Figure 8:
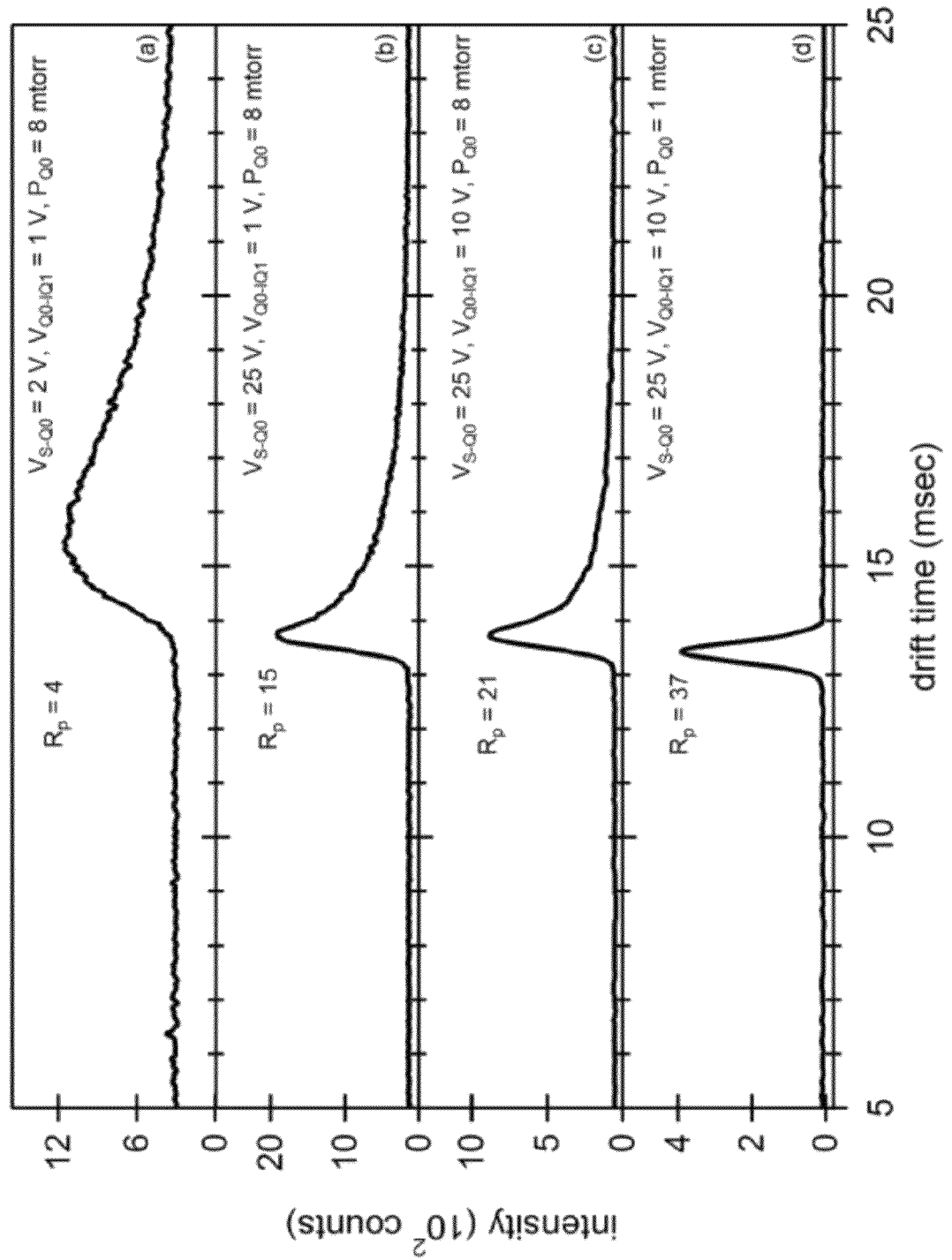
FIG. 8 shows mobility spectra acquired using the IMS/MS instrument. The spectra were acquired by varying the potential between the skimmer of the invention and Q0 ($V_{S-Q0}$), the potential between Q0 and IQ1 ($V_{Q0-IQ1}$), and the pressure in Q0 ($P_{Q0}$). The spectra show how the resolving power ($R_p$) of the measurement is affected as $V_{S-Q0}$ is increased from (a) 2 to (b) 25 V, $V_{Q0-IQ1}$ is increased from (b) 1 to (c) 10 V, and $P_{Q0}$ is decreased from (c) 8 to (d) 1 mtorr.

A series of mobility spectra obtained using different operating parameters for the Q0 region of the mass spectrometer in the IMS/MS instrument is shown in FIG. 8. The operating parameters optimized include the potential between the skimmer and Q0 ($V_{S-Q0}$), the potential between Q0 and IQ1 ($V_{Q0-IQ1}$), and the pressure in Q0 ($P_{Q0}$). The potential between the skimmer and Q0 was increased and the pressure in Q0 was decreased by replacing the original skimmer in the standard configuration of the mass spectrometer with the modified skimmer of the invention. The resolving power ($R_p$), which is a quantification of the separation capability of a mobility measurement, was calculated using the equation: $R_p = (t_d/w_{0.5})$. Where $t_d$ is the drift time and $w_{0.5}$ is the temporal peak width at half-height of the mobility peak.

The mobility spectra show that the resolving power of the measurement increases from 4 to 37 as $V_{S-Q0}$ is increased from 2 to 25 V and $P_{Q0}$ is decreased from 8 to 1 mtorr. The increase in the resolving power of the mobility measurement is attributed to a decrease in the effect of collisional focusing on the ion packet at increased electric field strengths and decreased pressures in the Q0 region. Specifically, at lower electric field strengths and higher pressures, the ion packet is slowed to near thermal velocities by collisions with the background gas in Q0. While this condition focuses the trajectory of the ions onto the central axis of Q0 and increases the transmission of the ions into the mass analyzer, it also causes the distribution of the ions in the ion packet to diffuse along the axis of Q0, resulting in a broad asymmetric profile. However, when the electric field strength is increased and the pressure is decreased, the ions transit Q0 at an increased velocity and therefore are not readily focused onto and diffused along the axis of the quadrupole. This increase in velocity and decrease in diffusion is confirmed by the shift of the peaks in the mobility spectra to shorter drift times and more symmetrical profiles as $V_{S-Q0}$ and $V_{Q0-IQ1}$ were increased and $P_{Q0}$ was decreased.

The resolving power at a $V_{S-Q0}$ of 25 V and a $P_{Q0}$ of 1 mtorr is 37, a value that is similar to the resolving power of the IMS instrument before being interfaced to the mass spectrometer, indicate that the broadening of the ion packet due to collisional focusing under these operating parameters is effectively zero. Accordingly, a $V_{S-Q0}$ of 25 V and a $P_{Q0}$ of 1 mtorr are the optimum operating parameters for obtaining a mobility spectrum using an IMS/MS instrument. These optimized operating parameters are easily attained in the mass spectrometer of the IMS/MS instrument using the modified skimmer of the invention.

Figure 9:
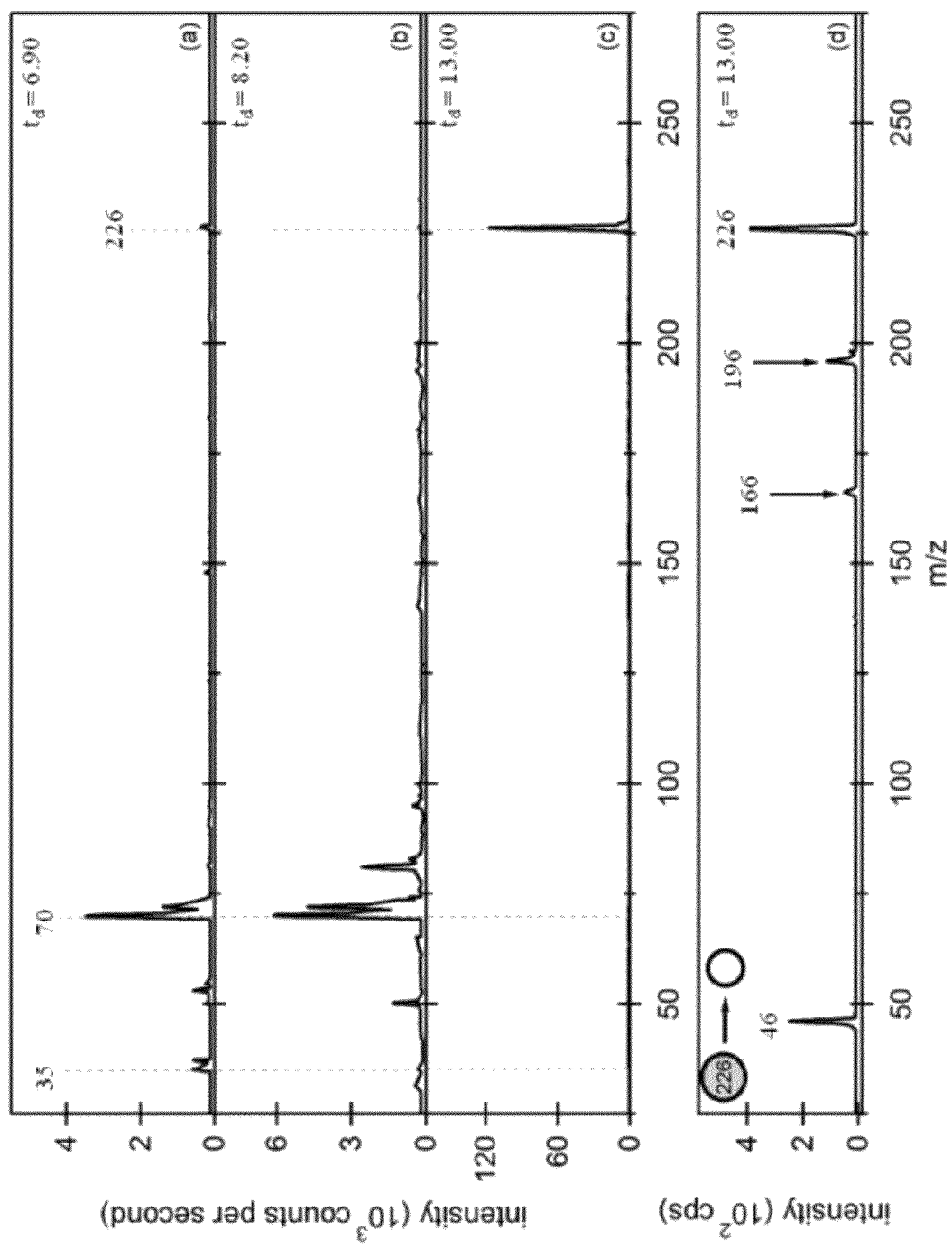
FIG. 9 shows mass and tandem mass spectra obtained using the IMS/MS instrument operated in the selected mobility monitoring dual-gate mode. Plot (a) is the mass spectrum when a drift time of 6.90 msec was monitored, plot (b) is the mass spectrum when a drift time of 8.20 msec was monitored, plot (c) is the mass spectrum when a drift time of 13.00 msec was monitored, and plot (d) is the tandem mass spectrum when a drift time of 13.00 msec and a m/z of 226 was monitored.

A series of mass and tandem mass spectra obtained by operating the IMS/MS instrument in the selected mobility monitoring dual gate mode are shown in FIG. 9. In the selected mobility monitoring mode, the ion gate in the IMS is opened for a finite period of time to allow a packet of ions into the drift region of the IMS while the ion gate in the differentially pumped interface of the mass spectrometer is opened after a specified time delay for the same duration as the first ion gate. The time delay is selected to permit only the portion of the ion packet with a desired drift time (or mobility) to pass into the mass spectrometer. The mass spectra indicate that the ion species with drift times of 6.90 and 8.20 msec have m/z values of 35, 37, 53, 55, 70, 72, and 74 where as the ion species with a drift time of 13.00 msec has a m/z value of 226. The tandem mass spectrum indicates that the collision-induced dissociation pathway for the ion species with a drift time of 13.00 msec and a m/z of 226 is the loss of m/z 30 and 46 from the product ion. Overall, the addition of ion beam gating capabilities to the differentially pumped interface of the mass spectrometer using the modified skimmer of the invention allows for highly selective measurements to be made using the IMS/MS instrument.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions and types of materials described herein are intended to define the parameters of the invention, they are by no means limiting, but are instead exemplary embodiments.

Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the terms "comprising" and "wherein." Moreover, in the following claims, the terms "first," "second," and "third," are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," "more than" and the like include the number recited and refer to ranges which can be subsequently broken down into subranges as discussed above. In the same manner, all ratios disclosed herein also include all subratios falling within the broader ratio.

One skilled in the art will also readily recognize that where members are grouped together in a common manner, such as in a Markush group, the present invention encompasses not only the entire group listed as a whole, but each member of the group individually and all possible subgroups of the main group. Accordingly, for all purposes, the present invention encompasses not only the main group, but also the main group absent one or more of the group members. The present invention also envisages the explicit exclusion of one or more of any of the group members in the claimed invention.

The embodiment of the invention in which an exclusive property or privilege is claimed as follows:

1. An apparatus comprising:
   a COTS IMS, said COTS IMS having a thermal desorber, a radiation ion source, an electrostatic ion gate, an ambient pressure counter-flow drift region, a guard grid, and faraday plate detector;
   an atmospheric pressure interface, said atmospheric pressure interface fluidly coupled to the COTS IMS, said atmospheric pressure interface having an interface flange, an orifice electrode with pinhole, a focusing ring, a skimmer electrode, a radio frequency only quadrupole, a drift gas inlet, a vacuum pump and,
   a triple quadrupole COTS MS with electron multiplier detector, said triple quadrupole COTS MS fluidly coupled to the atmospheric pressure interface.

2. The apparatus as recited in claim 1 wherein the faraday plate detector is constructed to contain a centered hole with diameter of 6 mm.

3. The apparatus as recited in claim 1 wherein orifice electrode contains a pinhole with diameter of 250 µm.

4. The apparatus as recited in claim 1 wherein the skimmer contains a hole with diameter of 400 µm.

5. The apparatus as recited in claim 1 wherein the orifice aperture is located 4 mm from the skimmer aperture.

6. The apparatus as recited in claim 1 wherein the drift gas inlet provides a flow rate of 950 cc/min into the apparatus.

7. A method for coupling a COTS IMS to a COTS MS through modification of the atmospheric pressure interface comprising:

an interface flange, wherein said interface flange is used to attach the COTS IMS to the COTS MS;

a faraday plate with centered hole, wherein said faraday plate is positioned within the interface flange such that the faraday plate hole is aligned with the orifice pinhole;

a drift gas, wherein said drift gas is introduced into the apparatus via the interface flange between the faraday plate detector and orifice electrode and, a skimmer electrode, wherein said skimmer electrode is located between the initial and intermediate pumping stages of the atmospheric pressure interface, wherein said skimmer electrode is electrically isolated from all surrounding electrodes such that the voltages between the orifice and skimmer and between the skimmer and Q0 are tunable, wherein the hole size and length of said skimmer electrode is decreased such that the operating pressure in the intermediate pumping stage of the COTS MS is reduced.

8. The method of claim 7 whereby the hole in faraday plate is positioned 5 mm from the pinhole in the orifice.

9. The method of claim 7 whereby the drift gas flow into the apparatus is 950 cc/min, 350 cc/min which flows into the COTS IMS and 600 cc/min which flows in the COTS MS.

10. The method of claim 7 whereby a skimmer with a centered hole of 400 μm replaces the original skimmer in the COTS MS.

11. The method of claim 5 whereby the distance from the orifice to the skimmer is 6 mm.

12. The method of claim 7 whereby the voltage between the skimmer and Q0 is tunable to values above ±12 V.

13. The method of claim 7 whereby the pressure in the intermediate pumping stage of the COTS MS is tuned to a value of 1 mtorr.

14. A method for gating the ion beam in the atmospheric pressure interface between a COTS IMS and a COTS MS comprising:

electrically isolating the orifice and skimmer electrodes;

applying an alternating electric field between the orifice and skimmer electrodes;

obstructing the ion beam from passing into the COTS MS by applying a negative (or inverse) potential field gradient between the orifice and skimmer, and, passing the ion beam into the COTS MS by applying a positive potential field gradient between the orifice and skimmer.

15. The method of claim 14 whereby the voltage applied between the orifice and skimmer that is used to block the ion beam from entering the COTS MS is tuned to −40 V for negative ion detection and +40 V for positive ion detection.

16. The method of claim 14 whereby the voltage applied between the orifice and skimmer that is used to pass the ion beam from entering the COT MS is tuned to −10 V for negative ion detection and +10 V for positive ion detection.

* * * * *

UNITED STATES PATENT AND TRADEMARK OFFICE
CERTIFICATE OF CORRECTION

PATENT NO. : 8,536,518 B2  
APPLICATION NO. : 13/533564  
DATED : September 17, 2013  
INVENTOR(S) : Kazole Page 1 of 1

It is certified that error appears in the above-identified patent and that said Letters Patent is hereby corrected as shown below:

Title Page, Item (75) Inventor: Delete "NY" and insert --NJ--.

Signed and Sealed this  
Twenty-ninth Day of October, 2013

Teresa Stanek Rea  
*Deputy Director of the United States Patent and Trademark Office*